United States Patent
Bhagavatula et al.

(10) Patent No.: US 8,663,618 B2
(45) Date of Patent: Mar. 4, 2014

(54) SURFACE MODIFIED POROUS POLYMERS FOR ENHANCED CELL GROWTH

(75) Inventors: Prasad L. V. Bhagavatula, Pune (IN); Virginia D. Britto, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/583,841

(22) PCT Filed: Mar. 9, 2011

(86) PCT No.: PCT/IN2011/000158
§ 371 (c)(1),
(2), (4) Date: Nov. 26, 2012

(87) PCT Pub. No.: WO2011/111069
PCT Pub. Date: Sep. 15, 2011

(65) Prior Publication Data
US 2013/0059932 A1    Mar. 7, 2013

(30) Foreign Application Priority Data
Mar. 9, 2010 (IN) .............................. 535/DEL/2010

(51) Int. Cl.
*A61K 31/74* (2006.01)
*A61L 2/14* (2006.01)
*C08J 7/00* (2006.01)
*C08J 7/12* (2006.01)
*C08J 7/18* (2006.01)

(52) U.S. Cl.
USPC .......................... 424/78.26; 521/83; 525/386

(58) Field of Classification Search
USPC ........................... 424/78.26; 521/83; 525/386
See application file for complete search history.

(56) References Cited

U.S. PATENT DOCUMENTS

| 5,387,237 A | 2/1995 | Fournier et al. |
| 6,551,608 B2 | 4/2003 | Yao |

FOREIGN PATENT DOCUMENTS

| DE | 102006020728 A1 * | 11/2006 | ............... C09D 7/12 |
| JP | 06049247 A * | 2/1994 | ................. C08J 7/04 |

OTHER PUBLICATIONS

Sharma et al., "Silver nanoparticles: Green synthesis and their antimicrobial activities." Advances in Colloid and Interface Science, 145 (2009), pp. 83-96.*
Spencer, et al., "*Torulopsis bombicola* sp. n.," Antonie van Leeuwenhoek, 1970, pp. 129-133, vol. 36.
Gugala, et al., "Attachment, Growth, and Activity of Rat Osteoblasts on Polylactide Membranes Treated with Various Low-Temperature Radiofrequency Plasmas," Journal of Biomedical Materials Research Part A, 2006, pp. 288-299, vol. 76.
Ertel, et al., "Radiofrequency Plasma Deposition of Oxygen-Containing Films on Polystyrene and Poly(Ethylene Terephthalate) Substrates Improves Endothelial Cell Growth," Journal of Biomedical Materials Research, 1990, pp. 1637-1659, vol. 24.
Rau, et al., "Sophorolipids: A Source for Novel Compounds," Industrial Crops and Products, Jan. 2001, pp. 85-92, vol. 13.

(Continued)

*Primary Examiner* — Randy Gulakowski
*Assistant Examiner* — Kara Boyle
(74) *Attorney, Agent, or Firm* — Blank Rome LLP (57) ABSTRACT

A process for surface modification of polymer that enhances cell growth as well as inhibits growth of microorganisms is disclosed.

8 Claims, 5 Drawing Sheets

(56) References Cited

OTHER PUBLICATIONS

Singh, et al., "A Direct Method for the Preparation of Glycolipid-Metal Nanoparticle Conjugates: Sophorolipids as Reducing and Capping Agents for the Synthesis of Water Re-Dispersible Silver Nanoparticles and Their Antibacterial Activity," New Journal of Chemistry, Jan. 2009, pp. 646-652, vol. 33, No. 3.

* cited by examiner

Figure 1

1. Untreated PE scaffold
2. plasma treated
3. plasma + AuNPs
4. plasma + AuNPs+ lysine

SURFACE MODIFIED POROUS POLYMERS FOR ENHANCED CELL GROWTH

CROSS-REFERENCE TO RELATED APPLICATIONS

The present application is a national phase of International Patent Application No. PCT/IN2011/000158, filed Mar. 9, 2011, which claims priority to Indian Patent Application No. 0535/DEL/2010, filed Mar. 9, 2010, the entire disclosures of which are incorporated by reference herein.

FIELD OF INVENTION

The invention relates to the process for the preparation of surface modified polymers that enhance cell growth and inhibits growth of microorganisms

BACKGROUND AND PRIOR ART

Porous polyethylene (pPE) implants are well established medical products which have been in use for many years. The materials are biocompatible and are well accepted by the medical community. However, cell growth into these conventional pPE scaffolds is poor. Surface modification to the polymer has been tried to improve cell growth. Such approaches include surface modification by self assembled monolayer formation, functionalization through silane molecules, layer-by-layer assembly, nano-indentation and etching with various advantages and disadvantages.

Gugala et al in J. Biomed Mater Res A, 2006, 76, 288 uses various plasma to study the attachment characteristics of osteoblasts on nonporous and porous polylactide. They conclude that ammonia treatment resulted in highest number of attached cells, but a longer duration of this treatment may prove detrimental to the polymer and is therefore avoided.

U.S. Pat. No. 5,387,237 relates to a bioartificial implantable pancreas for the treatment of insulin dependent diabetes mellitus. The bioartificial organ for implantation comprises a biocompatible fibrous or foam matrix in the vascularizing chamber. The matrix material is composed of organic or inorganic material, the organic material selected from polyolefins such as polyethylene, polypropylene etc. which are non halogenated and non fluorinated. The matrix thickness thus allows sufficient absorption of proteins, ECM materials, growth factor materials, develop blood supply, and the matrix also is preferably non-absorbable by the body of the mammal and minimizes fibriotic overgrowth and encapsulation.

U.S. Pat. No. 6,551,608 relates to novel porous materials that possess antiviral and/or antimicrobial properties. The invention encompasses a porous material having antiviral or antimicrobial properties which is comprised of a porous substrate and an antiviral or antimicrobial agent to overcome the need for porous, non-fibrous materials that resist the accumulation or growth of viruses and/or microbes. The process of preparation of the novel particles comprises sintering of tie thermoplastic material with the antimicrobial agent.

Thus the prior art review clearly brings out a need in the art for compositions of polymer with enhanced cell growth properties. Further there is a need in the art to provide processes for preparing such compositions and identify the various Cells that can grow on such membranes.

Literature reports indicate that transition metals in ionic or metallic form posses antimicrobial action, exemplified herein in Ag ions, but are unstable, particularly in aqueous medium and cannot exert their antimicrobial action for a sustained period of time. In the instant invention, the objective is to provide a composition of a polymer that serves as a reservoir, it is necessary that there is a sustained action of an anti microbial agent to prevent formation of bio film. To overcome these drawbacks, the inventors propose a simple process of reducing Ag ions to nanoparticles and capping them using the same agent, thereby accomplishing the objective of providing sustained anti-microbial action and the polymer-anti microbial composition retaining it functionality as desired since the Ag nanoparticles are preventing formation of bio film.

OBJECTIVES OF THE INVENTION

The main objective of the invention is to provide the process for the preparation of surface modified polymers that enhance cell growth and inhibits growth of microorganisms.

Another objective of the invention is to provide a process for enhancement of cell growth.

Further an objective of the invention is to provide a surface treated polymer composition which can function as a medium for cell growth to occur, while simultaneously inhibiting microbial growth.

A further objective is to use the composition and process of the invention to make artificial body tissues and organs One more objective of the invention is to make shaped objects from the surface treated polymer that can function as reservoirs as mentioned above herein.

SUMMARY OF THE INVENTION

Accordingly, the present invention provides a process for the preparation of surface modified polymers that enhance cell growth and inhibits growth of microorganisms.

In an embodiment of the present invention, a process for the preparation of surface modified polymers, wherein said process comprising:
  a. providing plasma treated polymer;
  b. linking covalently sophorolipids of fatty acids to the plamsa treated porous polymer surface as obtained in step (a);
  c. exposing the polymer surface as obtained in step (b) to a solution of antimicrobial agent and boiling to reduce the ions of the antimicrobial to nanoparticles on the surfaces by the sophorolipids to obtain surface modified polymers.

In another embodiment of the present invention, sophorolipids used in step (b) are lipids derived from fatty acids and possessing a reducing sugar moiety, wherein said fatty acids are selected from, but not limited to stearic, oleic, linoleic and linolenic acids and said sugar moieties are preferably sophorose, rhamnose and trihalose.

In another embodiment of the present invention, polymer used in step (a) is selected from the group consisting of polyetherimide and polyethylene.

In another embodiment of the present invention, antimicrobial agent used in step (c) is silver nitrate.

In another embodiment of the present invention, said surface modified polymer enhances cell growth as well as inhibits growth of microorganisms.

In another embodiment of the present invention, plasma treated polymer of step (a) optionally further comprises attaching metal nanoparticles, preferably gold and attaching an amino acid to the metal nanoparticles to obtain surface modified polymer.

In another embodiment of the present invention, said amino acid is lysine.

DESCRIPTION OF DRAWINGS

FIG. 1.

DETAILED DESCRIPTION OF INVENTION

In the present invention, a composition of plasma treated polymer and functionalized metal nanoparticles is provided. Particularly, the composition comprises plasma treated polymer and an amino acid with at least two amine groups that functionalizes the metal nanoparticles. In one embodiment of the invention the composition comprises the amino acid and the plasma treated polymer.

The polymer of the invention is stable to plasma treatment. The polymer is optionally porous or non-porous. The preferred embodiments are porous polyethylene and polyetherimide.

The metal is selected from noble metal comprising the group selected from, but not limited to gold, silver, platinum and such like. In one embodiment of the invention, the composition comprises plasma treated polymer and nonmetals.

The plasma treatment is given using gases selected from $O_2$, $COO^-$, $N_2^-$, $NO_2^-$, $H_2$, $SO_2+H_2$, $NH_3$ and such like.

The functionalization of metal nanoparticles is carried out using amino acids with at least two amine groups, selected from but not limited to arginine, lysine and such like.

The process of the invention for preparing the composition of polymer, metal nanoparticles and their functionalization comprises:

1. The polymer surface is plasma treated using plasma, preferably $N_2$ and $H_2$ plasma,
2. Metal, preferably gold nano-particles are attached to the plasma treated surface and
3. Amino acid, preferably lysine molecules are attached to the gold nanoparticles.

Figure 1:
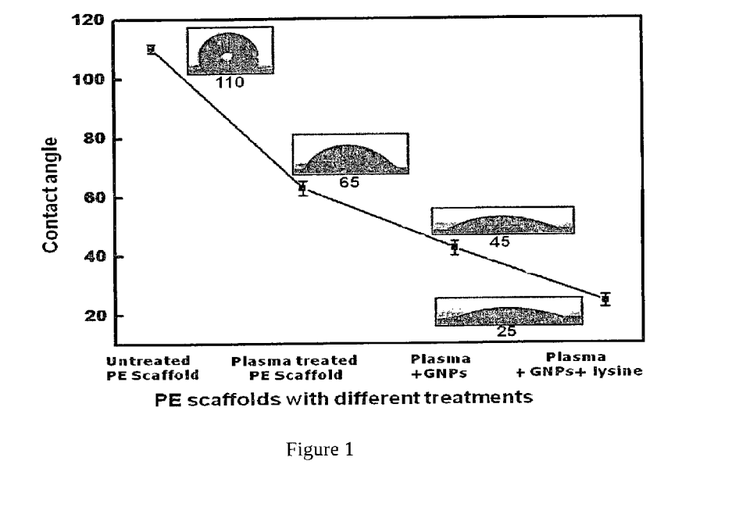
FIG. 1 is PE (polyethylene) scaffolds with different treatments. The figure depicts the water contact angle measured after each treatment. There is a clear indication that the contact angle decrease from 110 degrees (untreated) to 25 degrees (lysine treated)

The contact angle is initially 110 degrees, in step 1 the angel decreases to 65 degrees, with increase in cell growth, after step 2 the angle is poor at 45 degrees, to see a further decrease in angle to 25 degrees with cell growth being extremely high, please refer FIG. 1.

The composition of the polymer with surface modification should have improved integration of cells with improved anchorage and stability. The composition that enhances cell growth should also possess increased surface wettability and enhanced attachment and proliferation of cells on the surface.

In one embodiment of the invention, the plasma stable polymer is porous and is seeded with cells for its enhanced growth. In a preferred embodiment of the invention, the porous polymer is seeded with cells of the islets of Langerhans.

In the invention, a surface treated porous polymer composition with an antimicrobial agent is disclosed herein. The surface treated porous polymer composition with an antimicrobial agent aid in cell growth. The surface treated porous polymer composition with an antimicrobial agent aids in cell growth while simultaneously inhibiting the growth of microorganisms. The surface treated porous polymer composition with an antimicrobial agent comprises the polymer, antimicrobial agent and sophrolipids of fatty acids. The invention further discloses the process for the preparation of the surface treated porous polymer composition with an antimicrobial agent.

The process for the preparation of the surface treated porous polymer composition of the invention comprises the steps of:
a) treating the porous polymer with plasma;
b) linking covalently sophorolipids of fatty acids to the plamsa treated porous polymer surface and
c) exposing the polymer surface of step (b) to a solution of antimicrobial agent and boiling to reduce the ions of the antimicrobial to nanoparticles on the surfaces by the sophorolipids.

The polymer in the surface treated porous polymer-antimicrobial agent composition or the invention is any polymer, preferably polyethylene The antimicrobial agent of the invention is transition metal in ionic or metallic form, preferably silver nitrate, The plasma treatment options are selected from $N_2$ and $H_2$, oxygen, carbon di oxide, sulphur di oxide-hydrogen plasma and such like.

Lipid derived from fatty acids and possessing a reducing sugar moiety are the lipids of the. invention. The fatty acids are of the type but not limited to stearic, oleic, linoleic and linolenic acids. The sugar moieties are preferably sophorose, rhamnose, trihalose and such like.

The surface treated porous polymer-antimicrobial agent composition of the invention are fused network of particles and shaped objects formed of 400-1000 microns and having a pore size of 100-150 microns.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Plasma Treatment of PE Films

In a process for surface modification, pieces of PE scaffolds were exposed to plasma containing $H_2$ and $H_2$ gases. The plasma was excited by introducing hydrogen and nitrogen gases (ratio 7:3) into the electron cyclotron resonance (ECR) reactor chamber. The ECR plasma was excited by 245 GHz microwave source in $TE_{11}$ mode along with the required magnetic field of 875 Gauss generated by electromagnets. The ECR cavity consisted of a cylindrical stainless steel chamber, 15 cm in height and 12.5 cm in diameter and was coupled to the reactor chamber having a height of 30 cm and diameter of 20 cm. The reactor. chamber was facilitated with various ports like gas inlet vacuum port, sample holder port and feed-throughs. The 500 W microwave source was coupled, through a quartz window, to the resonance cavity. Base pressure was $10^{-6}$ mbar and operating pressure was $10^{-2}$ mbar. All films were washed well with ethanol before treatment. An exposure of 20 min introduced amine groups on the surface that would act as anchoring sites for the subsequent attachment of gold nanoparticles. (GNPs)

Example 2

Layering of GNPs

Each scaffold was washed twice or thrice with deionized water to remove any impurities present on the surface. Further the washed scaffolds were dipped in 70% alcohol for 15 min to ensure complete sterilization. These scaffolds were immersed in sterilized gold sol under aseptic conditions.

Example 3

Decoration of the GNP Layered Scaffolds with Lysine Molecules

A $10^{-4}$ M solution of lysine was prepared freshly in deionized water. The GNP layered scaffold was immersed in this solution and kept overnight to ensure complete attachment of lysine molecules to the exposed GNP surfaces.

Example 4

Cell Growth and Proliferation

CHO (Chinese Hamster Ovary cell line) cells were maintained and cultured in cell culture flasks (Falcon) containing Dulbecco's Modified Eagle's medium (DMEM) supplemented with 10% (v/v) foetal calf serum (FCS) and penicillin-streptomycin at 37° C. in a humidified 5% $CO_2$/95% air atmosphere. Cells were washed with phosphate-buffered saline (PBS), detached by trypsinization (0.5% trypsin solution) and collected by centrifugation. Thereafter, cells were resuspended in a known volume of medium to a final concentration of $10^5$ cells/mL. The doubling time of the cells was calculated by seeding the cells on substrates at a concentration of $10^5$ cells/mL and incubating them at 37° C. with 5% $CO_2$. In a typical experiment, each scaffold was washed thoroughly with deionized water, to remove any additional lysine molecules; sterilized with 70% alcohol, dried in the airflow of laminar chamber and was placed carefully in a 12 well culture plate. The treated side of the scaffolds was faced up. 100 μL of the resuspended cell suspension was seeded slowly onto the surface of the scaffolds. The cells were allowed to attach on the surface of the film and after 10-15 minutes, 1 mL of DMEM was added along the wall of the wells without disturbing the arrangement. The cells were incubated for 24h and 48h at 37° C. in humidified 5% $CO_2$/95% air atmosphere. Optical micrographs were taken at regular intervals to monitor the cell proliferation.

Example 5

Synthesis of Oleic Acid and Linoleic Acid Sophorolipids

Sophorolipids were prepared by biotransformation of fatty acids such as oleic acid and/or linoleic acid using *Candida bombicola, Yarrowia lipolytica, Candida apicola*, and *Candida bogoriensis* as described in Spencer, J. F. T.; Gorin, P. A. J.; Tulloch, A. P. Antonie Van Leeuwenhoek 1970, 36, 129.

Example 6

Fabrication of pPE Scaffolds

Figure 2:
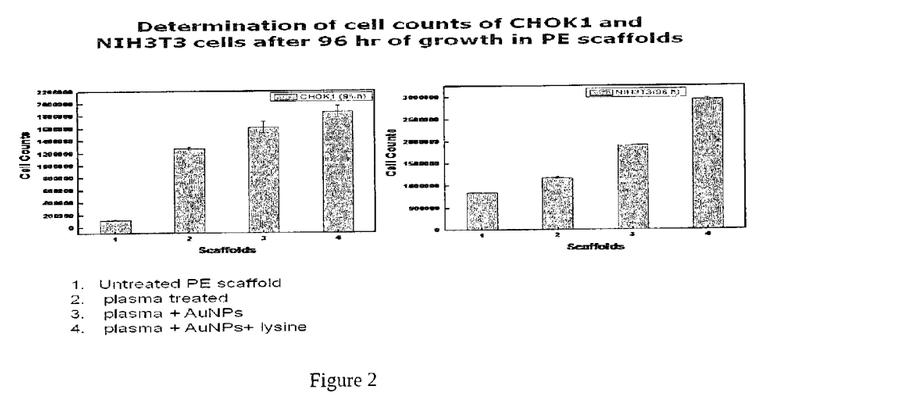
FIG. 2: The graph shows the cell counts obtained from differently treated scaffolds. The cells are trypsinized from the scaffolds after 96h of cell growth and counted in Neubauer's chamber.
Figure 3:
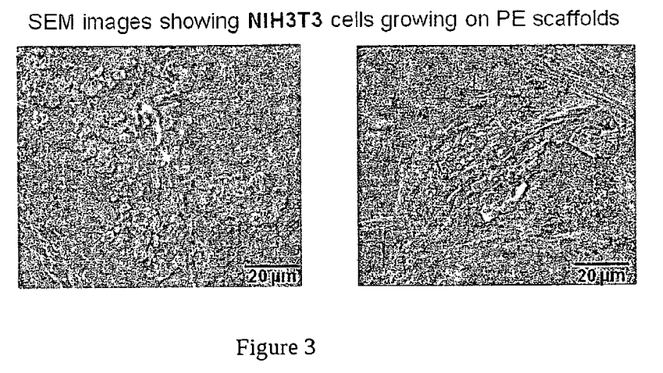
FIG. 3: The SEM images show NIH 3T3 cells growing in PE scaffolds. The cells are seeded at a density of $10^4$ cells/scaffold and allowed to grow for 96h, after which they were fixed by means of 4% PFA (para formaldehyde). These scaffolds are then viewed under SEM.
Figure 4:
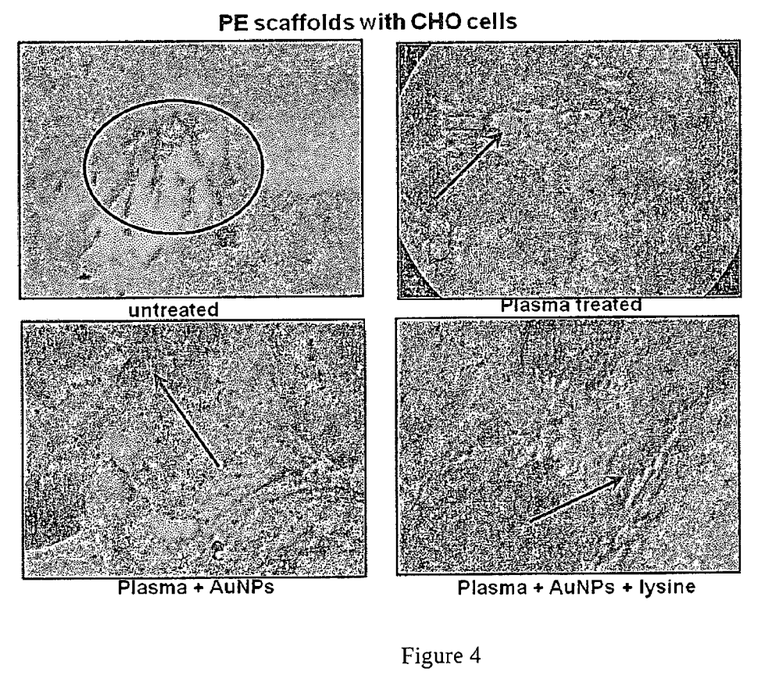
FIG. 4: The phase contrast images CHO cells growing in PE scaffolds. The cells are seeded at a density of $10^4$ cells/scaffold and allowed to grow for 96h, after which they are fixed by means of 4% PFA (para formaldehyde). These scaffolds are then viewed under 20× magnification.
Figure 5:
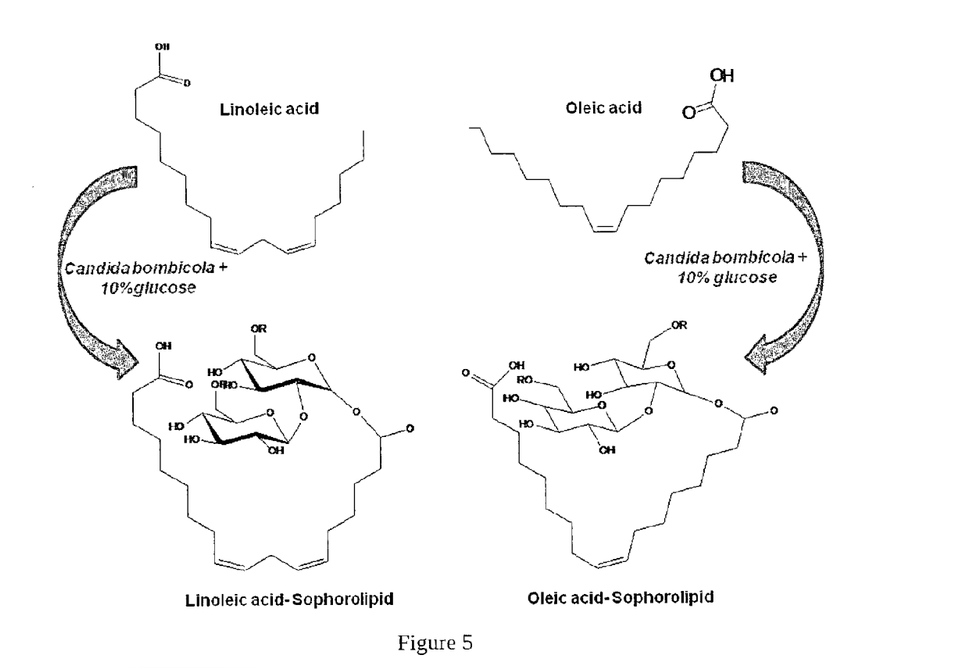
FIG. 5: Structure of oleic acid and linoleic acid along with their respective sophorolipids.
Figure 6:
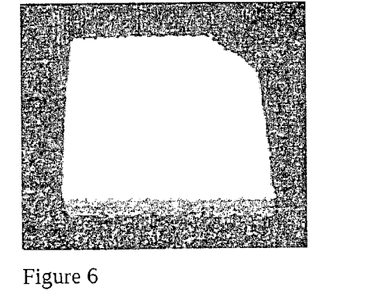
FIG. 6: Image of porous polyethylene scaffold
Figure 7:
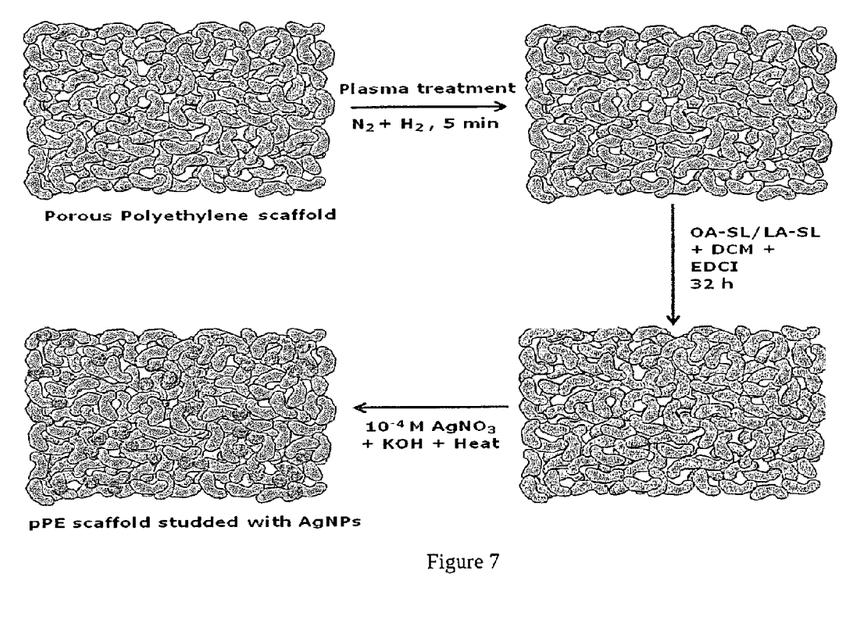
FIG. 7: Representation of the complete procedure followed to obtain silver nanoparticle studded porous polyethylene scaffolds.

Narrowly dispersed (s=log $D_{90}/D_{10}$=0.12) micro-pellets (median particle size, $D_{50}$~380 microns; average particle size ~426 microns) of linear high density polyethylene pellets of were sintered at 160° C. in custom made moulds, to give porous polyethylene scaffolds with an average pore size of ~208 microns and porosity ~46%. These porous polyethylene scaffolds were roughly comparable to the porous polyethylene scaffolds widely used in clinical practice primarily as implants in the maxilla-facial region. The result is as seen in FIG. 2, 3.

Example 7

Attachment of oleic acid sophorolipid (OA-SL) and linoleic acid (LA-SL) sophorolipid to the scaffold In the first step, the polymer scaffolds were treated with $N_2^-$ and $H_2$ plasma for 5 min. Thereafter, oleic acid sophorolipid (OASL)/linoleic acid sophorolipid (LASL) molecules were covalently stitched onto the scaffolds as described below. pPE scaffolds of 1.5 cm² size were taken in a round bottomed flask with 100 mg OA-SL/LA-SL in the presence of a 100/200 mg catalyst 1-ethyl-3-(3-dimethylamino propyl)-carbodiimide (EDCI) and 5 mL of dichloromethane (DCM)/dimethyl formamide (DMF) and refluxed for 32 h with continuous stirring. After the reaction is complete, the supernatant is decanted; the scaffolds are separated, washed with DCM/DMF/ethyl acetate several times and dried in a desiccator under vacuum.

Example 8

Formation of Silver Nanoparticles

The scaffolds, having OA-SL and LA-SL molecules chemically stitched onto their surface as seen in example 3 were exposed to 50 mL of $10^{-3}$ M $AgNO_3$ solution with 1 mL of 1M KOH (pH~11) under boiling condition. The $Ag^+$ ions were reduced and converted to silver nanoparticles by the SL molecules. As the SL(sophorolipid) molecules were covalently attached to the polymer scaffold, a silver nanoparticle studded 3D scaffold resulted. This is indicated by the development of a brownish colour on the otherwise white coloured scaffold.

Comparative Example

Control experiments containing untreated scaffolds and plasma treated scaffolds were also performed, which did not give any reduction of $Ag^+$ ions to $Ag^0$. This indicates that the chemically stitched SL molecules are the reducing as well as capping agents in this reaction.

Figure 8:
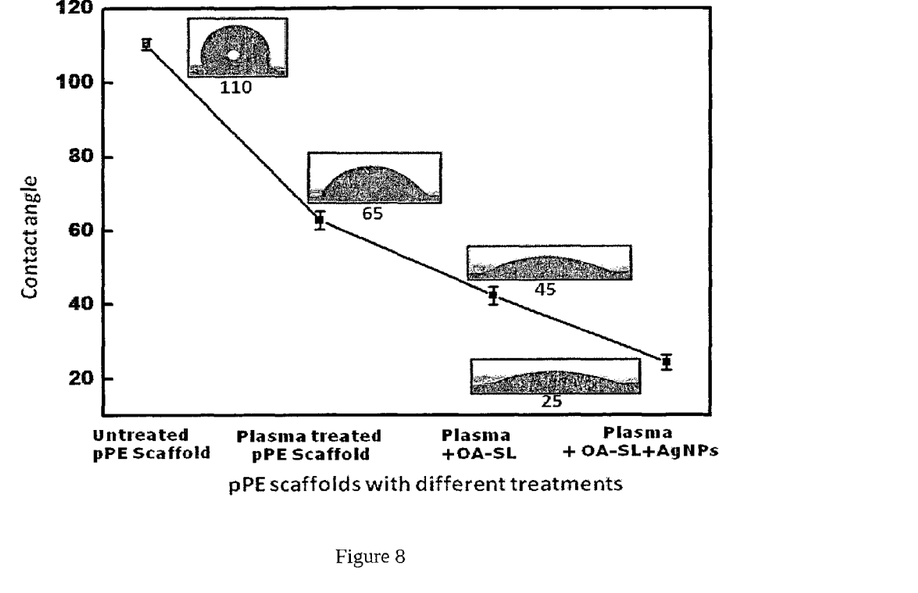
FIG. 8: Contact angle obtained after different treatments of pPE scaffolds

Water contact angles were measured at each level. FIG. 8 shows that the untreated pPE scaffold is highly hydrophobic with a contact angle of 110 degrees. This value goes on decreasing drastically as we treat the scaffolds with plasma and sophorolipids. Since these sophorolipids are bola-amphiphilic in nature, their presence on the scaffolds changes its surface from hydrophobic to hydrophilic. When the SL(sophorolipid) molecules are covalently stitched to the polymer surface, the reaction occurs between the —COOH group of the lipid and the —$NH_2$ group on the polymer surface exposing the other end of the lipid, namely, sophorose. This makes the surface hydrophilic and the same is reflected in the water contact angles which change from 110° (untreated polymer scaffold) to 65° (plasma treated) to 45° (SL attached). This further reduces to 25° after the in-situ formation of silver nanoparticles on the polymer scaffolds. This is a good indication as further studies on cell attachment and proliferation require the surface to be hydrophilic.

Example 9

Antibacterial Assay

All three micro organisms were maintained on Luria Bertani agar slants. Pre-inoculums of the above-mentioned bacterial strains were inoculated separately in 100 mL of Luria Bertani medium and incubated (30° C., 200 rpm) for 24 h in order to perform further experiments. Antibacterial tests of silver studded scaffolds were performed using standard dilution micro-method. The culture containing $10^8$ cfu/mL was serially diluted to obtain $10^4$cfu/mL. In a typical experiment, five test tubes containing LB broth containing $10^4$ cfu/mL, were incubated with untreated pPE scaffold, plasma treated pPE scaffold, OA-SL/LA-SL containing pPE scaffold and scaffold containing AgNPs. The fifth tube was incubated without any scaffold and served as a control. The whole setup was incubated at 37° C. under shaking conditions (200 rpm). Aliquots of 75 μL were drawn from each of the above said sets at regular intervals and plated on Luria-Bertini-Agar plates. These plates were also incubated at 37° C. for 24 h and the colonies were counted manually. Percentage of bacterial cell survival was calculated according to the following formula $$\% \text{ Cell survival} = 100 \times (N_e/N_c) \quad (1)$$

Figure 9:
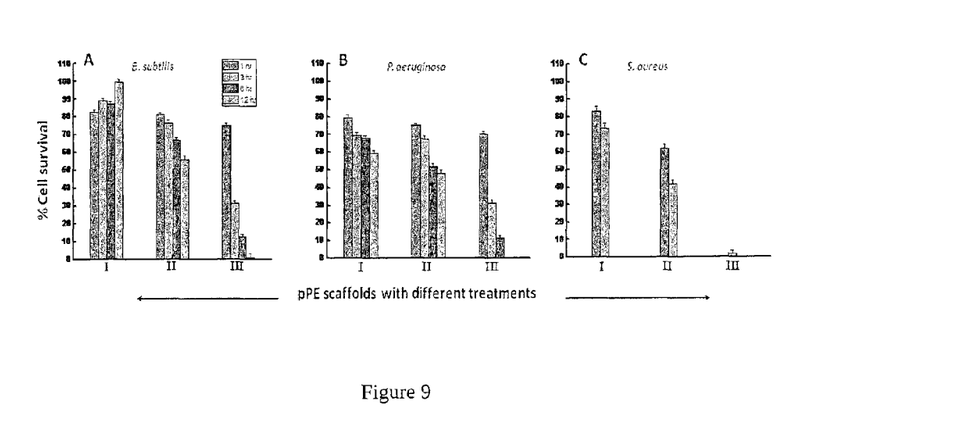
FIG. 9: Statistical data representing the % cell survival of *Bacillus subtilis* (A), *Pseudomonas aeruginosa* (B) and *Staphyloccocus aureus* (C) against ⊟) pPE-NH$_2$ scaffold; ⊟⊟) pPE-NH$_2$-SL scaffold and ⊟⊟⊟) pPE-NH$_2$-SL-Ag scaffold after different time intervals.

Where, $N_e$=Number of living bacterial colony on the examination plate $N_c$=Number of living bacterial colony on the control plate FIG. 9 referes to the statistical data representing the % cell survival of *Bacillus subtilis* (A), *Pseudomonas aeruginosa* (B) and *Staphyloccocus aureus* (C) against ⊟) pPE-$NH_2$ scaffold; ⊟⊟) pPE-$NH_2$-SL scaffold and ⊟⊟⊟) pPE-$NH_2$-SL-Ag scaffold after different time intervals.

Advantages:
1. The surface modified polymers enhance cell growth as well as inhibit growth of microorganisms.
2. The process of surface modification depends minimally on plasma treatment thus keeping the polymer intact to a large extent.
3. The process for surface modification of polymers offers a simple yet efficient process for providing a medium for cell growth.
4. The surface modified polymer can be used as scaffold for enhancement of cell growth of different types of cells.
5. The surface modified polymer can be further used to make shaped objects catering to the needs of a subject in need of such products.

We claim:

1. A process for the preparation of surface modified polymers, wherein said process comprising:
   a. providing plasma treated polymer;
   b. linking covalently sophorolipids of fatty acids to the plamsa treated polymer surface as obtained in step (a);
   c. exposing the polymer surface as obtained in step (b) to a solution of antimicrobial agent and boiling to reduce the ions of the antimicrobial to nanoparticles on the surfaces by the sophorolipids to obtain surface modified polymers.

2. The process as claimed in claim 1, wherein sophorolipids used in step (b) are lipids derived from fatty acids and possessing a reducing sugar moiety, wherein said fatty acids are selected from, but not limited to stearic, oleic, linoleic and linolenic acids and said sugar moieties are preferably sophorose, rhamnose and trihalose.

3. The process as claimed in claim 1, wherein polymer used in step (a) is selected from the group consisting of polyetherimide and polyethylene.

4. The process as claimed in claim 1, wherein antimicrobial agent used in step (c) is silver nitrate.

5. The process as claimed in claim 1 wherein said surface modified polymer enhances cell growth as well as inhibits growth of microorganisms.

6. The process of claim 1, wherein plasma treated polymer of step (a) optionally further comprises attaching metal nanoparticles, preferably gold and attaching an amino acid to the metal nanoparticles to obtain surface modified polymer.

7. The process as claimed in claim 6, wherein said amino acid is lysine:

8. The process as claimed in claim 6, wherein surface modified polymer enhance cell growth as well as inhibits growth of microorganisms.

* * * * *